US008119697B2

(12) United States Patent
Mechoulam et al.

(10) Patent No.: US 8,119,697 B2
(45) Date of Patent: Feb. 21, 2012

(54) ANTI-NAUSEA AND ANTI-VOMITING ACTIVITY OF CANNABIDIOL COMPOUNDS

(75) Inventors: Raphael Mechoulam, Jerusalem (IL); Linda Parker, Waterloo (CA); Aviva Breuer, Jerusalem (IL)

(73) Assignee: Yissum Research Development Company of the Hebrew University of Jerusalem, Jerusalem (IL)

( * ) Notice: Subject to any disclaimer, the term of this patent is extended or adjusted under 35 U.S.C. 154(b) by 1201 days.

(21) Appl. No.: 11/454,703

(22) Filed: Jun. 16, 2006

(65) Prior Publication Data

US 2007/0049645 A1    Mar. 1, 2007

Related U.S. Application Data

(63) Continuation of application No. 10/368,935, filed on Feb. 19, 2003, now abandoned.

(30) Foreign Application Priority Data

Feb. 19, 2002 (IL) .......................................... 148244

(51) Int. Cl.
*A01N 31/00* (2006.01)
*A61K 31/045* (2006.01)
(52) U.S. Cl. ...................................................... 514/724
(58) Field of Classification Search .................. 514/454, 514/724
See application file for complete search history.

(56) References Cited

U.S. PATENT DOCUMENTS

| 4,847,290 A | 7/1989 | Burstein |
| 5,434,295 A | 7/1995 | Mechoulam et al. |
| 5,874,459 A | 2/1999 | Makriyannis et al. |
| 6,113,940 A | 9/2000 | Brooke et al. |
| 6,162,829 A | 12/2000 | Burstein |
| 6,328,992 B1 | 12/2001 | Brooke et al. |
| 6,383,513 B1 | 5/2002 | Watts et al. |
| 6,403,126 B1 | 6/2002 | Webster et al. |
| 2002/0031480 A1 | 3/2002 | Peart et al. |

FOREIGN PATENT DOCUMENTS

| GB | 2 384 707 A | 8/2003 |
| GB | 2386322 | 9/2003 |
| WO | WO 93/05031 | 3/1993 |
| WO | WO 99/52524 | 10/1999 |
| WO | WO 01/03668 | 1/2001 |
| WO | WO 01/95899 | 12/2001 |
| WO | WO 01/95899 A2 | 12/2001 |
| WO | WO 01-98289 | 12/2001 |
| WO | WO 02/32420 | 4/2002 |
| WO | WO 02/32420 A1 | 4/2002 |
| WO | WO 02 064109 A | 8/2002 |
| WO | WO 02 069993 A | 9/2002 |
| WO | WO 03/037306 | 5/2003 |
| WO | WO 03/063847 A1 | 8/2003 |

OTHER PUBLICATIONS

Darmani et al., "The potent emetogenic effects of the endocannabinoid, 2-AG (2-arachidonoylglycerol) are blocked by delta-9-tetrahydrocannabinol and other cannabinoids," pp. 34-42; MEDLINE Abstract Acc. No. NLM11752094 of the Journal of Pharmacology and Experimental Therapeutics, vol. 300(1), Jan. 2002.
Darmani et al, "The endogeneous cannabinoid 2-arachidonoylglycerol induces vomiting: Blockade by marijuana and its synthetic analogs.", p. 2126; Biosis Abstract Acc. No. PREV200200002690 of Society for Neuroscience Abstracts vol. 27(2), Nov. 2001.
Parker, Linda A. et al., "Cannabidiol, a non-psychoactive component of cannabis and its synthetic dimethylheptyl homolog suppress nausea in an experimental model with rats." Neuroreport, England Apr. 16, 2002, vol. 13, No. 5, pp. 567-570 (XP009010573).
Adams, R. et al., "Structure of Cannabidiol XII. Isomerization to Tetrahydrocannabinols," Journal of the American Chemical Society, American Chemical Society, Washington, DC, vol. 63, 1941, pp. 2209-2213, (XP002208081).
Yamamoto I et al., "Recent advances in the metabolism of cannabinoids," International Journal of Biochemistry and Cell Biology 1995 United Kingdom, vol. 27, No. 8, 1995, pp. 741-746, (XP002241104).
Soderpalm, et al., "Antiemetic efficacy of smoked marijuana Subjective and behavioral effects on nausea induced by syrup of ipecac," Pharmacology, Biochemistry and Behavior 69 (2001),pp. 343-350.
Samara et al., "Pharmacokinetics of the dimethylheptyl homolog of cannabidiol in dogs," Drug Metabolism and disposition: biological fate of chemicals, 1988, vol. 16, No. 6, p. 875-879.
The United Kingdom Parliament, Select Committee on Science and Technology Ninth Report (Nov. 4, 1998) at http://www.parliament.the-stationery-office.co.uk/pa/Id199798/Idselect/Idsctech/151/15101.htm.
The United Kingdom Parliament, Select Committee on Science and Technology Second Report (Mar. 14, 2001) at http://www.publications.parliament. uk/pa/Id200001/Idselect/Idsctech/50/5001.htm.
Baek, et al., (1985) Boron Triflouride Etherate on Alimina. A Modified Lewis Acid Reagent. An Improved Synthesis of Cannabidiol Tetrahedron Letters. vol. 26, No. 8, pp. 1083-1086. Biosis Abstract Acct. No. PREV200200002690 of Society for Neuroscience Abstracts, vol. 27, No. 2, Nov. 2002, Darmani, N. A., "The endogenous cannabinoid 2-arachidonoylglycerol induces vomiting: Blockade by marijuana and its synthetic analogs," p. 2126.
Burstein, S.H. "The cannabinoid acids: Nonpsychoactive derivatives with therapeutic potential," *Pharmacology and Therapeutics* Apr. 1999; 82(1):87-96.
El-Darawy, et al. (Sep. 1972) Studies on Hashish, Isolation & Identification of Cannabinols and Effect of Certain Factors. Qual. Plant. Mater. Veg. XX1, 4, pp. 311-325.
Koch, KL. Illusory self-motion and motion sickness: a model for grain-gut interaction and nausea. DigDIS Sci. Aug. 1999, vol. 44, 8 Suppl. pp. 53S-57S, abstract submitted only.

(Continued)

*Primary Examiner* — Yong Chong
(74) *Attorney, Agent, or Firm* — Wolf, Greenfield & Sacks, P.C.

(57) ABSTRACT

The present invention relates the use of certain cannabidiol derivatives and of their dimethyl heptyl homologs (CBD-DMH) in the treatment of nausea, in particular chemotherapy-induced nausea, and of anti vomiting activity. The present invention relates also to the use of said cannabidiol derivatives being part of a pharmaceutical composition.

15 Claims, 2 Drawing Sheets

OTHER PUBLICATIONS

Molnar, J. et al., "Membrane associated antitumor effects of crocine-ginsenoside- and cannabinoid derivatives," *Anticancer Research* Mar. 2000; 20(2A):861-868.

Watanabe, et al. Inhibition of anandamide amidase activity in mouse brain microsomes by cannabinoids. Biol. Pharm. Bull. Aug. 1996, vol. 19, No. 8, pp. 1109-1111.

Yotoriyama, M. et al., "Comparison of pharmacological activity in mice of different cannabis extracts from CBDA and THCA strains," *Esei Kagaku* 1991; 37(6):507-511.

"Cannabinoid" at http://en.wikipedia.org/wiki/Cannabinoid, downloaded on Aug. 10, 2009 from Wikipedia, the free encyclopedia (12 pages).

Martin et al., *Mechanism of action of cannabinoids: how it may lead to treat of cachexia, emesis, and pain*. J. Support Oncol. Jul./Aug. 2004; 2:305-316.

Thomas et al., *Cannabidiol displays unexpectedly high potency as an antagonist of CB1 and CB2 receptor agonists in vitro.*, Br J Pharmacol. Mar. 2007; 150(5):613-623.

ANTI-NAUSEA AND ANTI-VOMITING ACTIVITY OF CANNABIDIOL COMPOUNDS

RELATED APPLICATIONS

This application is a continuation of Ser. No. 10/368,935, filed Feb. 19, 2003, now pending, which is herein incorporated by reference in its entirety.

FIELD OF THE INVENTION

The present invention relates the use of certain cannabidiol derivatives and of their dimethyl heptyl homologs (CBD-DMH) in the treatment of nausea and of anti vomiting activity.

BACKGROUND OF THE INVENTION

It is known that cannabidiol compounds of general formula I

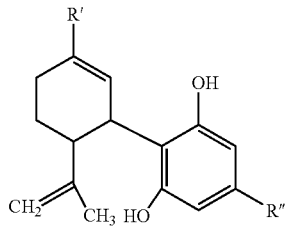

in which R' stands for $CH_3$ and R" stands for
a. straight or branched alkyl of 5 to 12 carbon atoms;
b. a group —O—R''', where R''' . . . is a straight or branched alkyl of 5 to 9 carbon atoms, or a straight or branched alkyl substituted at the terminal carbon atom by a phenyl group;
c. a group —$(CH_2)_n$—O-alkyl, where n is an integer from 1 to 7 and the alkyl group contains 1 to 5 carbon atoms, are antiinflammatory agents and have analgesic, antianxiety, anticonvulsive, neuroprotective, antipsychotic and anticancer activity.

There are known many cannabinoid-type compounds which have anti-nausea and anti-vomiting activity. However, many of them are psychoactive which is undesired for this purpose.

SUMMARY OF THE INVENTION

It has now been found that cannabidiol compounds of general formula I are not psychoactive but are very useful in the treatment of nausea and of anti-vomiting activity.

The present invention thus consists in the use of cannabidiol compounds of general formula I in the treatment of nausea and of vomiting activity. The compounds are used in particular in the treatment of chemotherapy-induced nausea.

Thus the invention provides methods for treating nausea and/or vomiting by administering to a subject in need of such treatment a cannabidiol compound as described herein. As used herein, a "subject" shall mean a human, a vertebrate mammal including but not limited to a dog, cat, horse, cow, pig, sheep, goat, or non-human primate, e.g., monkey, or a fowl, e.g., chicken. Included within the scope of the present invention are all animals which are susceptible to nausea and/or vomiting. The term "effective amount" of a cannabidiol compound (optionally combined with other non-cannabidiol compounds) refers to the amount necessary or sufficient to realize a desired biologic effect, e.g., a lessening of nausea and/or vomiting activity.

The cannabidiol compound of formula II and/or its DMH homolog of formula III may be used as such. It may also be used as part of a pharmaceutical preparation being selected among a tablet, a capsule, a granule, a suspension in a solution, etc.

Said pharmaceutical preparation may comprise in addition to the active ingredient an excipient selected among a carrier, a disintegrant, a lubricant, a stabilizer, a flavoring agent, a diluent, another pharmaceutically effective compound, etc.

The diluent may be an aqueous cosolvent solution comprising a pharmaceutically acceptable cosolvent, a micellar solution prepared with natural or synthetic ionic or nonionic surfactants, or a combination of such cosolvent and micellar solutions, etc.

The carrier may consist essentially of a solution of ethanol, a surfactant or water, or essentially of an emulsion comprising triglycerides, lecitin, glycerol, an emulsifier, an antioxidant, water, etc.

The present invention will hereinafter be described in detail without being limited by said description.

DETAILED DESCRIPTION OF THE INVENTION

Figure 1:
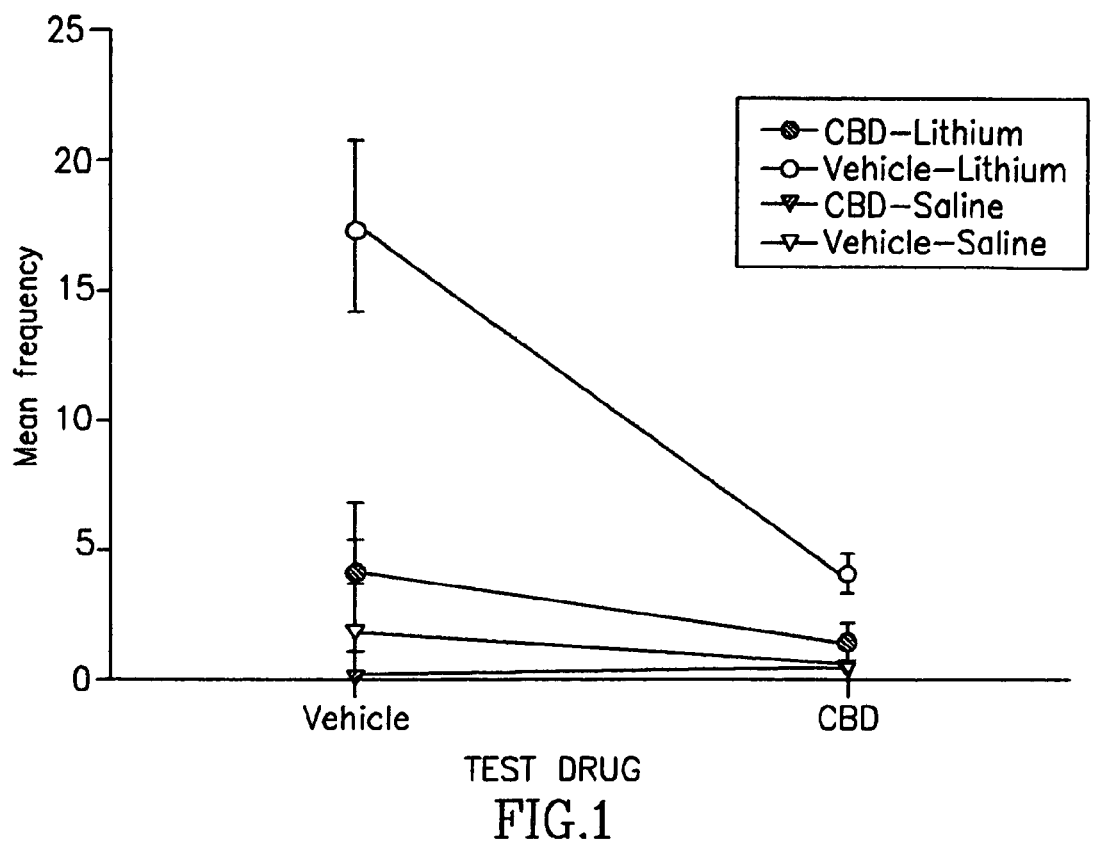
FIG. 1. Mean (+sem) frequency of conditioned rejection reactions elicited by a lithium- or saline-paired saccharin solution in Experiment 1 when rats were tested 30 min after an injection of vehicle or cannabidiol (CBD). The groups varied on the basis of the pretreatment drug (CBD or Vehicle) administered 30 min prior to an intraoral infusion of saccharin solution during the conditioning trial and the conditioning drug (Lithium or Saline) administered following saccharin exposure.

1) Materials and Methods
   a. Experiment 1 uses cannabidiol (CBD) of formula II:

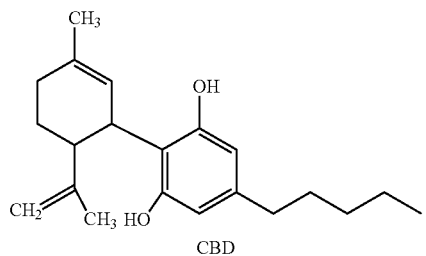

CBD

Experiment 2 uses cannabidiol-dimethyl heptyl (CBD-DMH) of formula III:

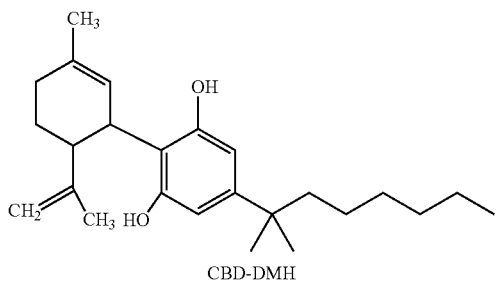

CBD-DMH

In Experiment 1 were used 29 male rats and in Experiment 2 were used 24 male Sprague-Dawley rats (Charles River Labs, St. Constant, Quebec), which weighed 290-350 gm on the conditioning day. They were individually housed in stainless steel hanging cages in a colony room kept at 21° C. on a 12:12 hr light:dark schedule with the lights on at 07.00 h. Throughout the experiment, the rats were maintained on ad-lib Purina Rat Chow and water. The procedures were approved by the Wilfrid Laurier University Animal Care Committee according to the guidelines of the Canadian Council on Animal Care.

b. The rats were surgically implanted with intra-oral cannulae as described by Parker, L. A. Learn Motiv., 13, 281-303 (1982). The surgical anesthesia preparation included administration of 0.4 mg/kg atropine solution i.p. 15 min prior to ketamine (75 mg/kg, i.p.) combined with xylazine (10 mg/kg, i.p.) which was dissolved in sterile water and administered at a volume of 1 ml/kg. On each of three subsequent days during recovery from surgery, the cannulae were flushed with a chlorhexidine rinse (Novlosan; 0.1% chlorhexidine) to prevent infection.

c. The design of the experiments evaluated the effect of CBD (Experiment 1) and of CBD-DMH (Experiment 2) on the establishment of conditioned rejection reactions, on the expression of conditioned rejection reactions during testing and the potential role of state dependent learning decrements in responding. The rats were randomly assigned to independent groups on the basis of the pretreatment drug and the conditioning drug. In Experiment 1, the groups were as follows: CBD-lithium (n=8), CBD-saline (n=6), Vehicle-lithium (n=8), Vehicle-saline (n=7). In Experiment 2, the groups were as follows: CBD-DMH-lithium (n=6), CBD-DMH-saline (n=6), Vehicle-lithium (n=6), Vehicle-saline (n=6). All rats were administered two test trials, one following an injection of the drug (Experiment 1: CBD; Experiment 2: CBD-DMH) and the other following an injection of the vehicle. $C_6H_{13}$ The order of the test trials was counterbalanced among the rats in each group.

d. CBD and CBD-DMH were prepared in a mixture (2.5 mg/ml Vehicle) of 1 ml alcohol/1 ml emulsifier/18 ml saline and were administered at a volume of 2 ml/kg. Lithium chloride was prepared in a 0.15 M (wt/vol) solution with sterile water and was administered at a volume of 20 ml/kg. All injections were intraperitoneally (ip) administered.

e. One week following the surgery, the rats were adapted to the conditioning procedure. On the adaptation trial, each rat was transported into the room that contained the Plexiglass test chamber (25 cm×25 cm×12 cm). The room as illuminated by four 25-W light bulbs located 30 cm from either side of the chamber. Each rat was placed individually into the test chamber, and a 30-cm infusion hose was then connected to the cannula through the ceiling of the chamber. A syringe was connected to the hose and placed into the holder for the infusion pump (Model 22; Harvard Apparatus, South Natick, Mass.). After 60 s, the pump delivered water through the tube into the rat's mouth at the rate of 1 ml/min for 2 min. The rat was then returned to its home cage.

f. The conditioning trial occurred on the following day; it was identical to the adaptation trial, except that the rats were infused with 0.1% saccharin solution rather than water. Thirty min prior to the conditioning trial, the rats were injected ip with either 2 ml/kg of the drug (CBD: Experiment 1; CBD-DMH: Experiment 2) or with the vehicle in which the drug was mixed. Immediately following the infusion of saccharin solution, the rats were injected ip with 20 ml/kg of lithium chloride or saline. During the intraoral infusion, the orofacial and somatic responses displayed by the rats were videotaped from a mirror mounted at a 45° angle beneath the test chamber. Immediately following the TR test, the rat was returned to its home cage.

g. The Taste Reactivity (TR) test trials were administered 4 and 6 days after the conditioning trial; on the day prior to the first test trial, the rats received an adaptation trial as described above. On each of two test trials, the rats were injected with either 5 mg/kg of the test drug (CBD: Experiment 1; CBD-DMH: Experiment 2) or with the vehicle, thirty min prior to receiving an infusion of saccharin solution for 2 min at the rate of 1 ml/min. The order of the tests was counterbalanced among the rats within each group. The orofacial and somatic reactions displayed by the rats were videotaped during the saccharin exposure.

h. In both experiments, on the day following the final TR test trial, the rats were administered a consumption test trial in a non-deprived state. On this trial, the water bottles were replaced with tubes containing the saccharin solution and the amounts consumed over a 6 hr period of drinking were recorded.

i. Taste reactivity scoring: A rater blind to the experimental conditions scored the videotapes on two occasions in slow motion (⅕ speed) using the Observer (Noldus, NL) event-recording program on a PC computer. The frequency of the rejection reactions of gaping (rapid large amplitude opening of the mandible with retraction of the corners of the mouth), chin rubbing (mouth or chin in direct contact with the floor or wall of the chamber and body projected forward) and paw treads (sequential extension of one forelimb against the floor or wall of the chamber while the other forepaw is being retracted) were summated to provide a rejection reaction score (inter-rater reliability: Experiment 1: Vehicle test r (29)= 0.91, CBD test r (29)=0.90; Experiment 2: Vehicle test r(24)=0.95; CBD-DMH test r (24)=0.97.

Figure 2:
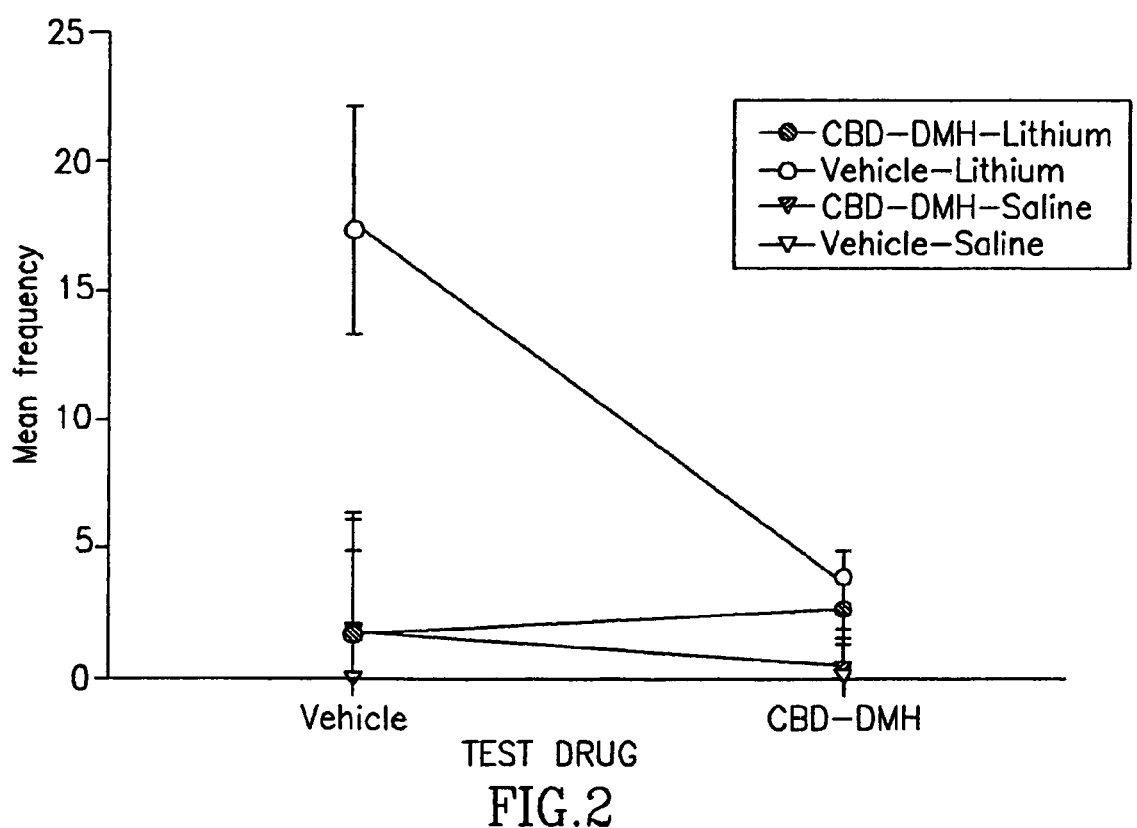
FIG. 2. Mean (+sem) frequency of conditioned rejection reactions elicited by a lithium- or saline paired saccharin solution in Experiment 2 when the pretreatment and test drug was cannabidiol dimethyllheptyl (CBD-DMH).

2) Results a. Taste Reactivity Test:

FIGS. 1 and 2 present as indicated above the mean frequency of rejection reactions displayed by the rats in the various groups during the vehicle test trial and during the drug (CBD: Experiment 1, CBD-DMH: Experiment 2) test trial. In both experiments, the pattern of responding indicates that the cannabinoid drug interfered with both the establishment of conditioned rejection and with the expression of previously established conditioned rejection reactions.

In Experiment 1 with CBD, the 2 by 2 by 2 mixed factor ANOVA revealed significant effects of pretreatment drug, $F(1, 25)=6.0$; $p=0.022$, conditioning drug, $F(1, 25)=10.9$; $p=0.003$, test drug, $F(1, 25)=7.4$; $p=0.012$, test drug by conditioning drug, $F(1, 25)=6.0$; $p=0.021$ and a pretreatment by conditioning drug interaction that approached statistical significance $F(1, 25)=3.6$; $p=0.069$. Subsequent Least Significant Difference (LSD) post-hoc pair-wise comparison tests [20] revealed that the lithium-conditioned rats, but not the saline-conditioned rats, displayed significantly fewer conditioned rejection reactions during the CBD test trial than during the vehicle test trial ($p$'s$<0.05$). This indicates that CBD attenuated the expression of previously established conditioned rejection reactions. Additionally, across both test drug conditions, the lithium-conditioned rats pretreated with CBD displayed fewer rejection reactions than those pretreated with vehicle ($p<0.05$) indicating that the CBD pretreatment during conditioning attenuated the establishment of conditioned rejection reactions, presumably by interfering with lithium-induced nausea.

In Experiment 2, with CBD-DMH, the 2 by 2 by 2 mixed factors ANOVA revealed a significant effect of test drug, $F(1, 20)=4.6$; $p=0.044$ and a significant pretreatment drug by conditioning drug by test drug interaction, $F(1, 20)=5.6$; $p=0.028$. Subsequent LSD post-hoc pair-wise comparison tests revealed that Group Vehicle-Lithium displayed significantly more rejection reactions during the vehicle test than any other group ($p$'s$<0.01$) and that this group displayed more rejection reactions during the vehicle test than during the drug test ($p<0.01$). CBD-DMH interfered with the establishment of conditioned rejection reactions when administered prior to a saccharin-lithium pairing and with the expression of these conditioning rejection reactions when administered prior to the subsequent test of conditioning.

Figure 3:
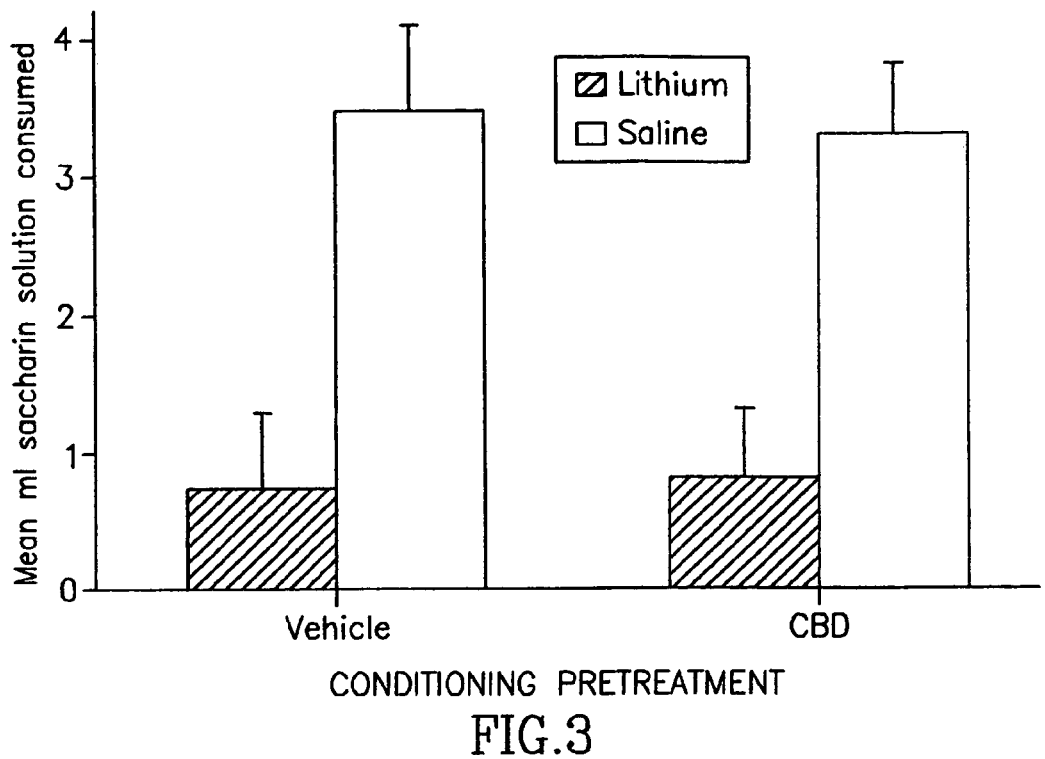
FIG. 3. Mean (+sem) ml consumed of lithium-paired or saline-paired saccharin solution during a 6 hr consumption test on the day following the final taste reactivity (TR) test trial among rats pretreated with 5 mg/kg of CBD or Vehicle prior to the conditioning trial in Experiment 1.
Figure 4:
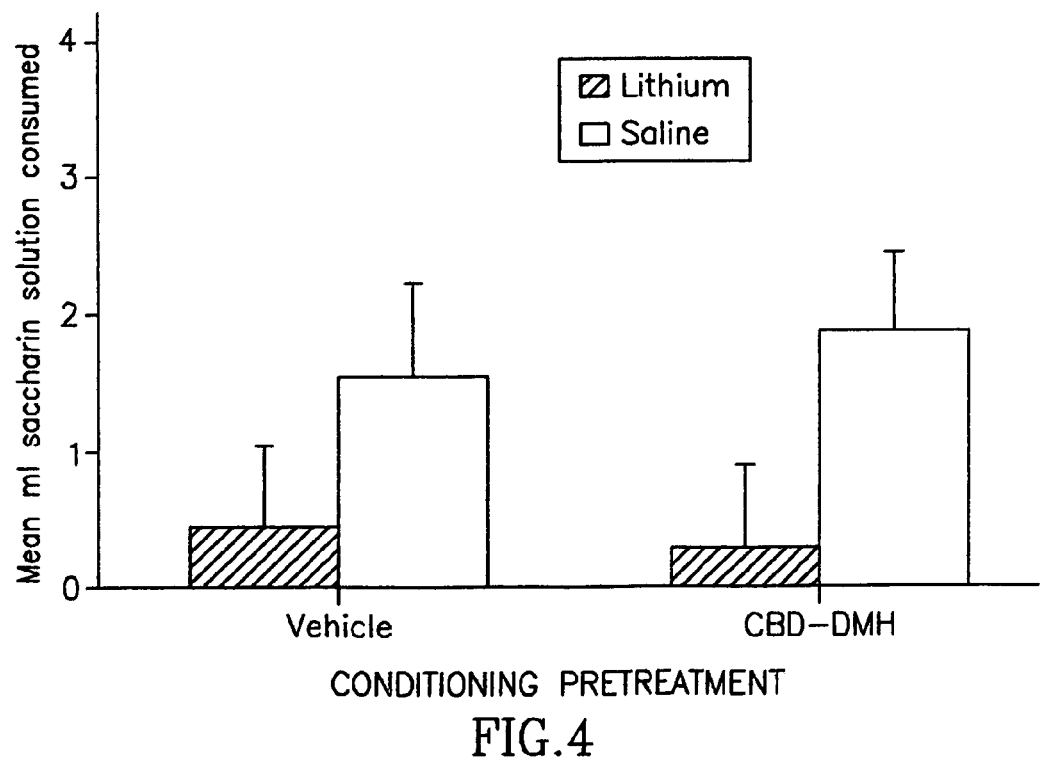
FIG. 4. Mean (+sem) ml consumed of lithium-paired or saline-paired saccharin solution during a 6 hr consumption test on the day following the final TR test trial among rats pretreated with 5 mg/kg of CBD-DMH or Vehicle prior to the conditioning trial in Experiment 2.

The attenuation of lithium-induced conditioned rejection reactions during conditioning or testing cannot be interpreted as state-dependent learning decrement, because when rats were trained and tested in the same cannabinoid sate, they displayed fewer rejection reactions than when they were trained and tested in the same vehicle state.

b. Consumption Test:

FIGS. 3 and 4 present the mean ml of saccharin solution consumed by the various groups in Experiments 1 and 2 respectively. As is apparent, rats suppressed their consumption of a lithium-paired saccharin solution, but pretreatment with CBD (Experiment 1) or CBD-DMH (Experiment 2) prior to conditioning did not modulate the strength of the avoidance response. A 2 by 2 ANOVA for each Experiment revealed only a significant effect of conditioning drug for Experiment 1 ($F(1,22)=25.01$; $p<0.001$) and a marginally significant effect of conditioning drug for Experiment 2 ($F(1, 19)=4.36$; $p=0.051$). There were no other significant effects.

3) Interpretation

The non-psychoactive cannabinoids, CBD and CBD-DMH, interfered with the establishment of conditioned rejection reactions (presumably by reducing the lithium-induced nausea) and with the expression of previously established conditioned rejection reactions (presumably by reducing conditioned nausea during the test). These results are the first to describe the anti-nausea properties of the naturally occurring cannabinoid, found in marijuana and its dimethylheptyl homolog. It has previously been reported similar effects produced by the 5HT3 antagonist anti-emetic agent, ondansetron, and THC; that is, both agents interfered with the establishment and the expression of conditioned rejection reactions in rats.

As has previously been reported using the antiemetic agent, ondansetron, as the pretreatment agent, CBD and CBD-DMH pretreatment did not interfere with the establishment of conditioned taste avoidance in a consumption test. Since treatments without emetic properties elicit taste avoidance, but not conditioned rejection reactions, taste avoidance does not reflect conditioned sickness. On the other hand, only treatments with emetic effects produce conditioned rejection reactions in rats suggesting that this affective change in taste palatability is mediated by nausea.

The anti-emetic effects of cannabinoid agonists, such as THC and WIN 55-212, appear to be mediated by specific actions at the CB1 receptor, because these effects are blocked by administration of the CB1 receptor antagonist, SR-141716. On the other hand, CBD and CBD-DMH have relatively weak affinity for the CB1 receptor and may be act by preventing the uptake of the endogenous cannabinoid agonist, anandamide. Further research is necessary to determine the specific mechanism by which CBD and CBD-DMH prevent nausea in rats.

4) CONCLUSION

The above results demonstrate that the non-psychoactive component of marijuana, cannabidiol, and its synthetic analog, cannabidiol dimethylheptyl, interfere with nausea and with conditioned nausea in rats.

Therapeutically effective amounts of cannabidiol compounds and homologs can be determined from animal models as described above and as will be well known to and routinely performed by one of ordinary skill in the art. The applied dose can be adjusted based on the relative bioavailability and potency of the administered compound. Adjusting the dose to achieve maximal efficacy based on the methods described above and other methods as are well-known in the art is well within the capabilities of the ordinarily skilled artisan.

All references that are recited in this application are incorporated in their entirety herein by reference.

What is claimed is:

1. A method for the treatment of nausea and of vomiting, comprising administering to a subject an effective amount of a cannabidiol compound of formula II:

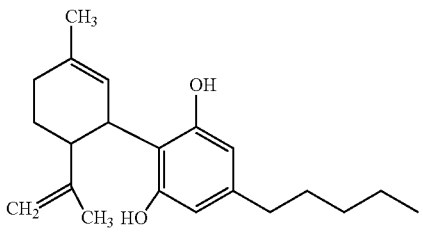

or Formula III:

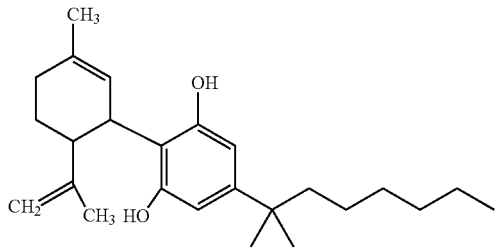

wherein the cannabidiol compound is used in particular in the treatment of chemotherapy-induced nausea, and wherein the cannabidiol compound is administered orally or parenterally.

2. The method of claim 1, wherein the cannabidiol compound is cannabidiol (CBD).

3. The method of claim 1, wherein the cannabidiol compound is the dimethyl heptyl homolog of cannabidiol (CBD-DMH).

4. The method of claim 1, wherein the cannabidiol compound is part of a pharmaceutical preparation being selected from the group consisting of a tablet, a capsule, a granule, and a suspension in a solution.

5. The method of claim 1, wherein the cannabidiol compound comprises in addition to the active ingredient one or more of the following: a carrier, a disintegrant, a lubricant, a stabilizer, a flavoring agent, a diluent, or another pharmaceutically effective compound.

6. The method of claim 5, wherein the diluent is an aqueous cosolvent solution comprising a pharmaceutically acceptable cosolvent, a micellar solution prepared with natural or synthetic ionic or nonionic surfactants, or a combination of such cosolvent and micellar solutions.

7. The method of claim 2, wherein the cannabidiol is part of a pharmaceutical preparation being selected from the group consisting of a tablet, a capsule, a granule, and a suspension in a solution.

8. The method of claim 7, wherein said pharmaceutical preparation comprises in addition to the active ingredient one or more of the following: a carrier, a disintegrant, a lubricant, a stabilizer, a flavoring agent, a diluent, or another pharmaceutically effective compound.

9. The method of claim 8, wherein the diluent is an aqueous cosolvent solution comprising a pharmaceutically acceptable cosolvent, a micellar solution prepared with natural or synthetic ionic or nonionic surfactants, or a combination of such cosolvent and micellar solutions.

10. The method of claim 3, wherein the dimethyl heptyl homolog of cannabidiol (CBD-DMH) is part of a pharmaceutical preparation being selected from the group consisting of a tablet, a capsule, a granule, and a suspension in a solution.

11. The method of claim 10, wherein said pharmaceutical preparation comprises in addition to the active ingredient one or more of the following: a carrier, a disintegrant, a lubricant, a stabilizer, a flavoring agent, a diluent, or another pharmaceutically effective compound.

12. The method of claim 11, wherein the diluent is an aqueous cosolvent solution comprising a pharmaceutically acceptable cosolvent, a micellar solution prepared with natural or synthetic ionic or nonionic surfactants, or a combination of such cosolvent and micellar solutions.

13. The method of claim 5, wherein the carrier comprises one or more of the following: ethanol; a surfactant; water; or an emulsion comprising triglycerides, lecithin, glycerol, an emulsifier, an antioxidant or water.

14. The method of claim 8, wherein the carrier comprises one or more of the following: ethanol; a surfactant; water; or an emulsion comprising triglycerides, lecithin, glycerol, an emulsifier, an antioxidant or water.

15. The method of claim 11, wherein the carrier comprises one or more of the following: ethanol; a surfactant; water; or an emulsion comprising triglycerides, lecithin, glycerol, an emulsifier, an antioxidant or water.

\* \* \* \* \*